United States Patent
Ravi et al.

(10) Patent No.: US 12,419,534 B2
(45) Date of Patent: *Sep. 23, 2025

(54) SYSTEM AND METHOD FOR MAGNETIC OCCULT LESION LOCALIZATION AND IMAGING

(71) Applicant: Stryker Corporation, Kalamazoo, MI (US)

(72) Inventors: Ananth Ravi, Toronto (CA); John Dillon, Mississauga (CA)

(73) Assignee: Stryker Corporation, Portage, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/712,365

(22) Filed: Apr. 4, 2022

(65) Prior Publication Data

US 2023/0023448 A1 Jan. 26, 2023

Related U.S. Application Data

(63) Continuation of application No. 16/331,888, filed as application No. PCT/CA2017/051054 on Sep. 8, 2017, now Pat. No. 11,291,384.

(Continued)

(51) Int. Cl.
*A61B 5/06* (2006.01)
*A61B 34/20* (2016.01)
(Continued)

(52) U.S. Cl.
CPC .............. *A61B 5/062* (2013.01); *A61B 34/20* (2016.02); *A61B 90/39* (2016.02);
(Continued)

(58) Field of Classification Search
CPC . A61B 5/062; A61B 90/39; A61B 2034/2051; A61B 2034/2055;
(Continued)

(56) References Cited

U.S. PATENT DOCUMENTS

| 4,622,644 A | 11/1986 | Hansen |
| 5,255,688 A | 10/1993 | Gilliard |

(Continued)

FOREIGN PATENT DOCUMENTS

| WO | 01/08578 A1 | 2/2001 |
| WO | 2006/056739 A2 | 6/2006 |
| WO | 2016/068700 A1 | 5/2016 |

OTHER PUBLICATIONS

Decision to Grant mailed Jul. 4, 2024, directed to EP Application No. 17847853.3; 2 pages.

(Continued)

*Primary Examiner* — Sean D Mattson
(74) *Attorney, Agent, or Firm* — Morrison & Foerster LLP

(57) ABSTRACT

Systems and methods for marking the location and extent of an anatomical region-of-interest, such as a tumor, using magnetic seeds whose position and orientation are measured or otherwise detected using a detection device that includes two or more magnetic sensors are described. One or more magnetic seeds are implanted to mark and define the center and extent of an anatomical region-of-interest and a magnetic sensor-based detector system is used to accurately identify the location of the magnetic seeds.

10 Claims, 4 Drawing Sheets

Related U.S. Application Data

(60) Provisional application No. 62/385,945, filed on Sep. 9, 2016.

(51) Int. Cl.
   - *A61B 90/00* (2016.01)
   - *A61M 37/00* (2006.01)
   - *G01R 33/00* (2006.01)
   - *G01R 33/02* (2006.01)
   - *G01V 3/08* (2006.01)
   - *G01V 3/12* (2006.01)

(52) U.S. Cl.
   CPC ..... *A61M 37/0069* (2013.01); *G01R 33/0005* (2013.01); *G01R 33/0047* (2013.01); *G01R 33/02* (2013.01); *G01V 3/08* (2013.01); *G01V 3/081* (2013.01); *G01V 3/12* (2013.01); *A61B 2034/2051* (2016.02); *A61B 2034/2055* (2016.02); *A61B 2034/2063* (2016.02); *A61B 2090/3908* (2016.02); *A61B 2090/3954* (2016.02); *A61B 2090/3958* (2016.02); *A61B 2090/3987* (2016.02)

(58) Field of Classification Search
   CPC .... A61B 2034/2063; A61B 2090/3908; A61B 2090/3954; A61B 2090/3958; A61B 2090/3987; A61B 34/20; A61B 90/00; A61B 5/05; A61M 37/0069; G01R 33/0005; G01R 33/0047; G01R 33/02; G01V 3/08; G01V 3/081; G01V 3/12
   See application file for complete search history.

(56) References Cited

U.S. PATENT DOCUMENTS

| | | | |
|---|---|---|---|
| 6,082,366 A | 7/2000 | Andra et al. | |
| 6,168,780 B1 | 1/2001 | Andrae | |
| 6,216,028 B1 | 4/2001 | Haynor et al. | |
| 6,263,230 B1 * | 7/2001 | Haynor | A61B 34/20 600/424 |
| 6,577,237 B1 | 6/2003 | Dames | |
| 7,561,051 B1 | 7/2009 | Kynor et al. | |
| 8,862,200 B2 | 10/2014 | Sherman et al. | |
| 9,459,087 B2 | 10/2016 | Dunbar et al. | |
| 11,291,384 B2 * | 4/2022 | Ravi | A61B 5/062 |
| 2003/0153827 A1 | 8/2003 | Ritter et al. | |
| 2007/0015960 A1 | 1/2007 | Gornert et al. | |
| 2007/0078334 A1 | 4/2007 | Scully et al. | |
| 2008/0039676 A1 | 2/2008 | Fischell et al. | |
| 2008/0058637 A1 | 3/2008 | Fischell et al. | |
| 2011/0227569 A1 | 9/2011 | Cai et al. | |
| 2012/0041297 A1 | 2/2012 | McGary | |
| 2013/0179117 A1 | 7/2013 | Delbaere et al. | |
| 2014/0018663 A1 | 1/2014 | Harmer et al. | |
| 2016/0051164 A1 | 2/2016 | Derichs et al. | |
| 2016/0354178 A1 * | 12/2016 | Mayes | A61B 90/39 |

OTHER PUBLICATIONS

Extended European Search Report mailed Apr. 21, 2020, directed to EP Application No. 17847853.3; 7 pages.

Extended European Search Report mailed Jan. 13, 2025, directed to EP Application No. 24190950.6; 10 pages.

Intention to Grant mailed Feb. 27, 2024, directed to EP Application No. 17847853.3; 7 pages.

International Preliminary Report on Patentability mailed Mar. 12, 2019, directed to International Application No. PCT/CA2017/051054; 7 pages.

International Search Report and Written Opinion mailed Dec. 21, 2017, directed to International Application No. PCT/CA2017/051054; 10 pages.

Notice of Allowance mailed Jan. 9, 2024, directed to CN Application No. 201780068548.1; 3 pages.

Notice of Allowance mailed Jun. 4, 2024, directed to CA Application No. 3,036,142; 1 page.

Office Action mailed Dec. 5, 2022, directed to CN Application No. 201780068548.1; 27 pages.

Office Action mailed Jul. 27, 2023, directed to CN Application No. 201780068548.1; 30 pages.

Office Action mailed Jun. 30, 2021, directed to JP Application No. 2019-513405; 12 pages.

Office Action mailed May 10, 2022, directed to JP Application No. 2019-513405; 4 pages.

Office Action mailed Oct. 27, 2023, directed to CA Application No. 3,036,142; 3 pages.

Ravi et al., U.S. Notice of Allowance and Fee(s) Due mailed Nov. 24, 2021, directed to U.S. Appl. No. 16/331,888; 10 pages.

Ravi et al., U.S. Office Action mailed Jun. 8, 2021, directed to U.S. Appl. No. 16/331,888; 16 pages.

Third Party Observations mailed Jul. 8, 2024, directed to EP Application No. 17847853.3; 15 pages.

Communication of a Notice of Opposition dated May 8, 2025, directed to EP Application No. 17847853.3; 93 pages.

* cited by examiner

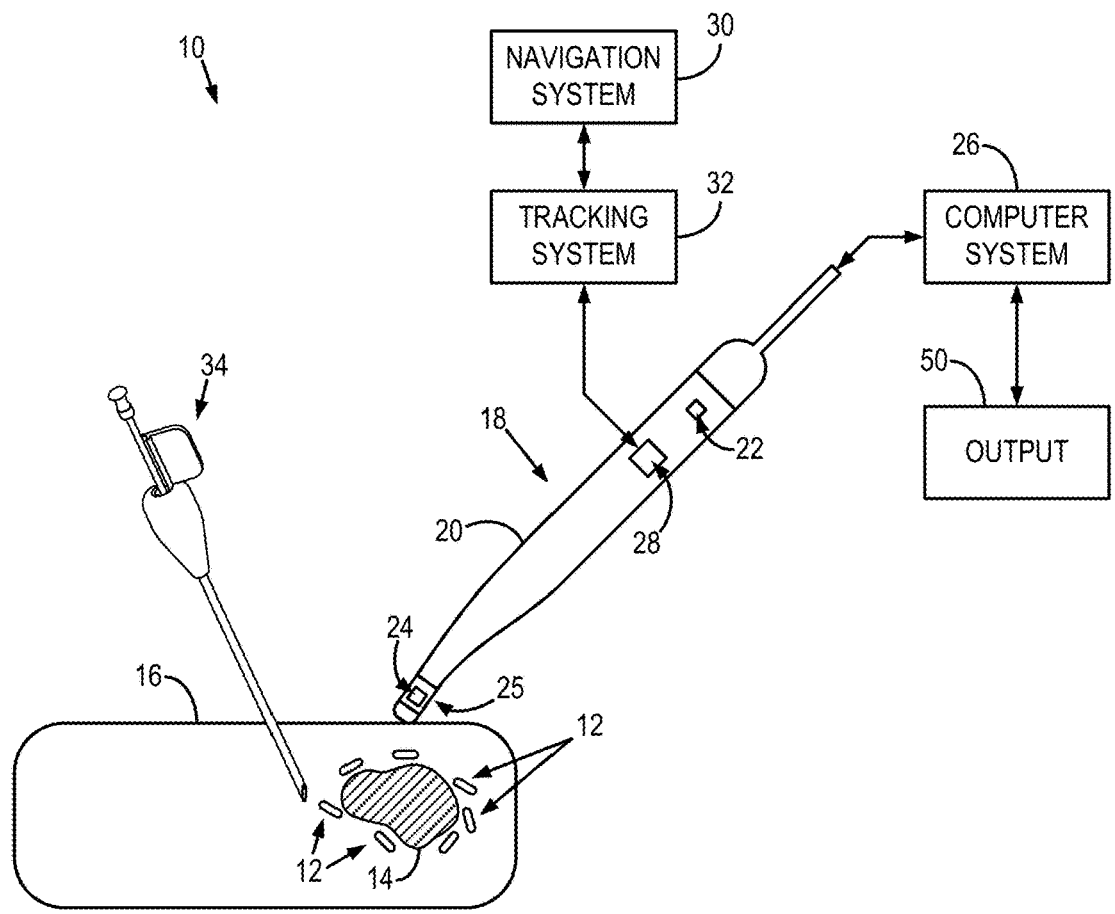
FIG. 1
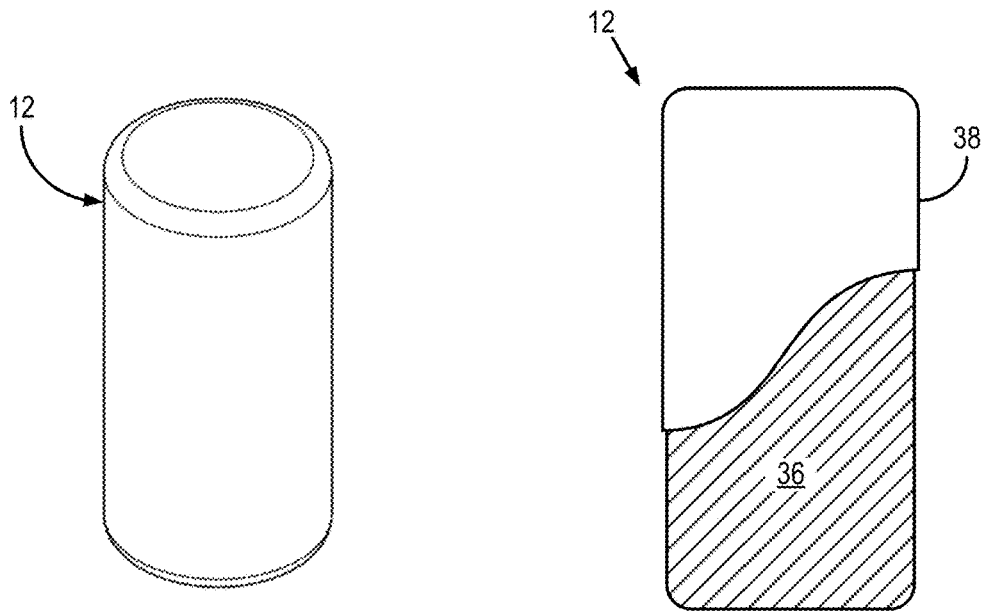
FIG. 2
FIG. 3

SYSTEM AND METHOD FOR MAGNETIC OCCULT LESION LOCALIZATION AND IMAGING

CROSS-REFERENCE TO RELATED APPLICATIONS

This application is a continuation of U.S. patent application Ser. No. 16/331,888, filed on Mar. 8, 2019, which is a National Phase of International Application No. PCT/CA2017/051054, filed on Sep. 8, 2017, which claims the benefit of U.S. Provisional Patent Application No. 62/385,945, filed on Sep. 9, 2016, and entitled "SYSTEM AND METHOD FOR MAGNETIC OCCULT LESION LOCALIZATION AND IMAGING," each of which are herein incorporated by reference in their entirety.

BACKGROUND

In contemporary breast cancer management, greater than 70 percent of breast cancer patients are eligible for and select breast-conserving therapy. The combination of early detection from screening and improvements in adjuvant therapies has translated into improvements in overall survival. However, the patient experience and treatment efficiency during the therapeutic process requires dramatic improvement.

Breast conserving surgery typically includes a surgical procedure whereby the tumor and a rim of surrounding normal tissue are removed. Currently, options for guiding the accurate excision of non-palpable lesions are unsatisfactory in terms of patient experience, healthcare system resource utilization, and cost-effectiveness. The main two approaches used for guidance of breast conserving surgery are wire localized breast biopsy ("WLBB") and radioactive seed localization ("RSL").

WLBB involves the implantation of a hooked wire on the day of surgery under mammographic or ultrasound guidance to mark the center and/or borders of the lesion. The patient is required to remain in the hospital with the wire protruding from the breast for several hours with minimal anesthetic. This is not only painful for the patient, but can also cause wires to dislodge as the patient waits for excision. Furthermore, if the wire is implanted under mammographic compression, the positioning of the wire rarely corresponds with supine surgical orientation, and its trajectory often requires surgical incision placement that is suboptimal for cosmesis. The path of the wire often results in the excision of more tissue than necessary.

RSL has more recently been adopted as an alternative approach to WLBB where a radioactive seed is used to mark the center and/or borders of the tumor. The implanted seeds are contained entirely within the breast, thereby preventing their movement with respect to the lesion. The surgeon uses a hand-held gamma ray detector to localize the seed and guide excision. While this addresses many of the patient flow and comfort issues with WLBB, the main obstacle with this technique is that the implanted seeds are radioactive, therefore requiring significant investment and vigilance for handling equipment, regulatory approvals and monitoring, specialized personnel and training, as well as administrative expenses. This process is also associated with marginally increased radiation exposure of staff and patients.

Thus, there remains a need for a system and method for guiding breast conserving surgeries, and other surgical excisions and procedures, in which less invasive, non-radioactive localization of the lesion or tumor are implemented.

SUMMARY OF THE DISCLOSURE

The present disclosure provides a magnetic detector system for localizing a magnetic seed that generates a magnetic field. The detector system generally includes a detector probe, a processor, and an output. The detector probe can include a housing extending along a central axis from a distal end to a proximal end, a first magnetic sensor arranged at the proximal end of the housing, and a second magnetic sensor arranged at the distal end of the housing. The first magnetic sensor and the second magnetic sensor detect a magnetic field generated by a magnetic seed and in response thereto generate signal data representative of the magnetic field. The processor can be in communication with the first magnetic sensor and the second magnetic sensor to receive the signal data therefrom and to process the signal data to compute a location of the magnetic seed. Processing the signal data includes accounting for an anisotropic geometry of the magnetic field generated by the magnetic seed. The output provides feedback to a user based on the computed location of the magnetic seed.

The present disclosure also provides a kit for localization of an implantable magnetic seed. The kit generally includes an introducer device, a detector probe, a processor, and an output. The introducer device includes a needle and a plunger. The needle is composed of a non-magnetic material and has a lumen that extends from a distal end to a proximal end of the needle. The lumen of the needle is sized to receive a magnetic seed for implantation in a subject. The plunger is also composed of a non-magnetic material and is arranged within the lumen of the needle. The plunger is sized to be received by the lumen of the needle such that when the plunger is translated along a length of the lumen air is allowed to flow past the plunger so as not to generate a vacuum effect in the lumen. The detector probe includes a housing extending along a central axis from a distal end to a proximal end, a first magnetic sensor arranged at the proximal end of the housing, and a second magnetic sensor arranged at the distal end of the housing. The first magnetic sensor and the second magnetic sensor detect a magnetic field generated by the magnetic seed and in response thereto generate signal data representative of the magnetic field. The processor is in communication with the first magnetic sensor and the second magnetic sensor to receive the signal data therefrom and to process the signal data to compute a location of the magnetic seed. Processing the signal data includes accounting for an anisotropic geometry of the magnetic seed. The output provides feedback to a user based on the computed location of the magnetic seed.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is made therefore to the claims and herein for interpreting the scope of the invention.

BRIEF DESCRIPTION OF THE DRAWINGS

FIG. 1 is a block diagram of an example magnetic occult lesion localization and imaging ("MOLLI") system.

FIG. 2 is an example of a magnetic seed that can be localized with the MOLLI system of the present disclosure.

FIG. 3 is an example of the magnetic seed illustrating a bio-compatible coating over a magnetic material core.

DETAILED DESCRIPTION

Figure 4:
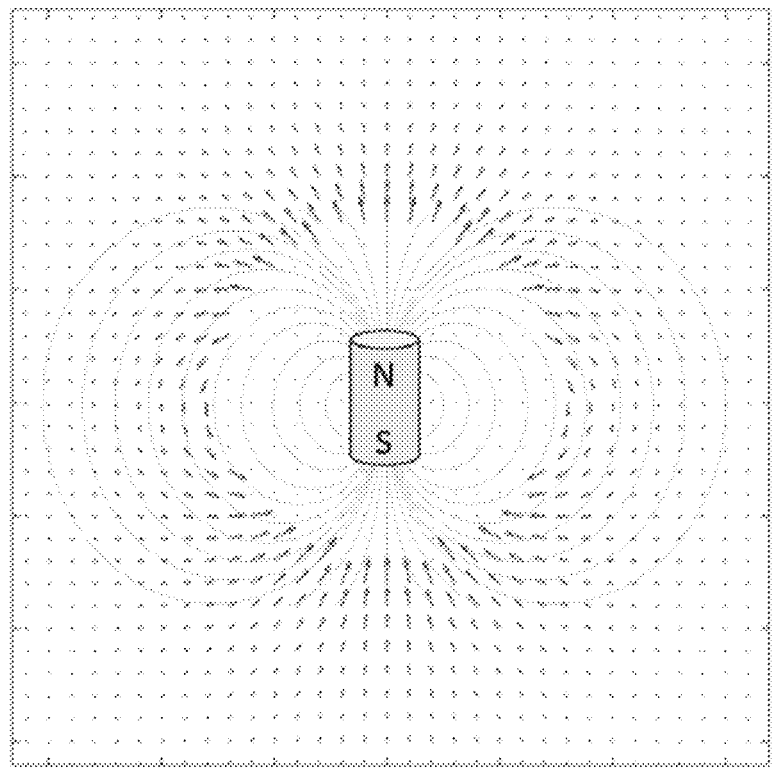
FIG. 4 is an example magnetic vector field diagram for a magnetic seed that generates an anisotropic magnetic vector field.

Described here are systems and methods for marking the location and extent of an anatomical region-of-interest, such as a tumor, using magnetic seeds whose position and orientation are measured or otherwise detected using a detection device that includes two or more magnetic sensors. The system described here generally includes magnetic seeds that are implanted into a subject to mark the center, boundaries, or both, of an anatomical region-of-interest, such as a tumor. In one example application, the magnetic seeds can be implanted to mark the boundary of a breast tumor; however, other clinical applications will be apparent to those skilled in the art.

According to the systems and methods of the present disclosure, one or more non-radioactive, magnetic seeds are implanted to mark and define the center and extent of an anatomical region of interest, such as a tumor or other lesion. Using a magnetic sensor-based detector system, a clinician (e.g., a surgeon) can accurately identify the location of the magnetic seeds prior to any incision. In use for marking the location of a breast tumor, the clinician can plan out a surgery to allow for the best achievable cosmetic result, while ensuring optimal oncologic outcomes.

As shown in FIG. 1, an example magnetic occult lesion localization and imaging ("MOLLI") system 10 is shown. The system 10 generally includes one or more magnetic seeds 12 that are implanted into an anatomical region-of-interest 14 in a subject 16. The region-of-interest 14 may include a tumor. In some embodiments, one or more of the magnetic seeds 12 may also be positioned on a skin surface of the subject 16.

A detector probe 18 is used to detect or otherwise measure the position, orientation, or both, of the magnetic seeds 12. The detector probe 18 generally includes a housing 20 that contains a first magnetic sensor 22 and a second magnetic sensor 24. The housing 20 generally defines a hand-held structure such that the detector probe 18 can be held and used by a clinician in an operating room or other surgical or clinical environment. As one example, the housing 20 can generally extend from a proximal end to a distal end along an axis. The first magnetic sensor 22 can be positioned or otherwise arranged at the proximal end of the house 20 and the second magnetic sensor 24 can be positioned or otherwise arranged at the distal end of the housing. In some embodiments, the first magnetic sensor 22 and the second magnetic sensor 24 can be coaxially aligned along the axis of the detector probe 18; however, in other embodiments one of the sensors (e.g., the second magnetic sensor 24) can be offset from the axis of the housing 20 to provide a more ergonomic design of the detector probe 18.

In some embodiments, the tip 25 of the detector probe 18 containing the second magnetic sensor 24 can be removable. In these configurations, the tip 25 can be interchanged with different tips having different magnetic sensors. For instance, as will be described below, one tip could include a single magnetic sensor while another tip could include more than one magnetic sensor, such as an array set of two or more magnetic sensors. Having a removable tip 25 also allows for easier sterilization since the tip 25 can be removed and separately sterilized rather than sterilizing the entire detector probe 18. In some other implementations, the tip 25 can be made disposable, such that after a single use the tip 25 can be removed and replaced with a new, sterile tip 25. In still other implementations, the detector probe 18 itself can be made to be disposable.

The detector probe 18 may also include other sensors, including additional magnetic sensors or one or more accelerometers, gyroscopes, temperature sensors, and so on. These other sensors can be positioned within the housing 20, or may be positioned or otherwise arranged on an outer surface of the housing. As one example, one of these other sensors could be affixed to the outer surface of the housing 20.

The detector probe 18 is in electrical communication with a computer system 26, which generally operates the detector probe 18 and receives signal data from the magnetic sensors 22, 24. The computer system 26 can also provide visual feedback, auditory feedback, or both, to a surgeon to assist the surgeon during a procedure. This feedback can be provided via an output 50, which may include a display, a speaker, or so on. It is contemplated that the MOLLI system 10 can be integrated with or otherwise implement virtual reality systems, augmented reality systems, or both.

As one non-limiting example of visual feedback that can be provided to a user, the output 50 can include a display that displays one or more numerical values associated with the detected location of a magnetic seed 12. For instance, the numerical values can represent distances between the detector probe 18 and a magnetic seed 12, an error or uncertainty in the measured location of a magnetic seed 12, or both.

As another non-limiting example of visual feedback that can be provided to a user, the output 50 can include a display to provide visual feedback integrating diagnostic images of the subject and the anatomical site to which magnetic seeds 12 will be or have been delivered. Examples of such diagnostic images include mammographic or other x-ray images, sonographic images, magnetic resonance images, or other images that may be organized in a central electronic repository, such as a picture archiving and communication system ("PACS"). In some implementations, the output 50 can include a display that provides a comparative view of diagnostic images and information from the signal data received from the magnetic sensors 22, 24. As one example, the computer system 26 can generate display elements indicating the position and orientation of the magnetic seeds 12, the detector probe 18, or both, and can display these display elements overlaid on the diagnostic images.

As one non-limiting example of auditory feedback that can be provided to a user, the output 50 can include a speaker that receives an auditory signal from the computer system 26. The auditory signal can indicate the presence of a magnetic seed 12 within the vicinity of the detector probe 18. For instance, a characteristic of the auditory signal can change based on the relative distance between the detector probe 18 and the magnetic seed 12. As one example, the pitch of the auditory signal can be changed. As another example, the auditory signal can include a series of chirps or other tones, with the repetition frequency of the chirps increasing or decreasing based on the relative distance between the detector probe 18 and the magnetic seed 12.

The computer system 26 can include one or more processors for receiving the signal data from the magnetic sensors 22, 24 and for processing the signal data to detect or otherwise measure a position, orientation, or both, of the magnetic seeds 12. In some embodiments, the computer system 26 can include one or more processors that are arranged within the housing 20 of the detector probe 18; however, in other configurations the computer system 26 is physically separate from the detector probe 18. The computer system 26 can also measure an error in the measured position, orientation, or both, of a magnetic seed 12 and can present this information to a user, such as by generating a visual, textual, or numerical display based on the measured uncertainty. The computer system 26 can also calibrate the detector probe 18, and process the signal data to provide an assessment of the margin of the region-of-interest 14 (e.g., a tumor margin) or to implement bracketing of the region-of-interest 14.

In some embodiments, the detector probe 18 may also include one or more trackers 28 used for tracking the detector probe 18 with a surgical navigation system 30. Examples of such sensors include optical markers, infrared emitters, radio frequency emitters, ultrasound emitters, and so on, which may be detected by a suitable tracking system 32, such as an optical tracking system, radio frequency tracking system, and so on. The trackers 28 may also include accelerometers, gyroscopes, and the like, for tracking the detector probe 18 using a surgical navigation system that is based on inertial sensors.

An introducer 34 is also provided for introducing the magnetic seeds 12 into the subject 16. The introducer 34 has a generally non-magnetic construction, such that the introducer 34 does not interfere with accurate placement of the magnetic seeds 12.

The MOLLI system 10 utilizes the magnetic sensors 22, 24 in the detector probe 18 to accurately locate the magnetic seeds 12 within a patient. Signal data measured by these magnetic sensors 22, 24 contain information about the magnetic field vector of the detected magnetic seeds 12, and this signal data is provided to the computer system 26 where the signal data are converted into a distance measure and visual feedback, auditory feedback, or both, to guide the surgeon.

It is contemplated that the MOLLI system 10 can detect a magnetic seed 12 that is around 7 cm from the tip of the detector probe 18. Based on this data, at a distance of 60 mm, magnetic seeds 12 can be detected with a one percent false positive/false negative rate. This added confidence will help ensure surgeons are able to accurately identify the target site.

An example magnetic seed 12 that can be implemented in accordance with the present disclosure is illustrated in FIGS. 2 and 3. In the example shown in FIG. 2, the magnetic seed 12 has a generally cylindrical shape; however, it will be appreciated that any other suitable shapes can be implemented, including spherical shapes, ellipsoidal shapes, rectangular shapes, and so on. Each magnetic seed 12 can be sized to fit in standard needles for implantation. As will be described below, a non-magnetic introducer device 34 can be used to accurately implant magnetic seeds 12.

In general, the magnetic seeds 12 are constructed such that they generate an anisotropic magnetic field. In some embodiments, the magnetic seeds 12 also generate magnetic fields with anisotropic magnetic flux density distributions.

The magnetic seeds 12 are generally composed of a magnetic material 36 that is encapsulated in a bio-compatible shell 38, as shown in FIG. 3. In some embodiments, the magnetic material is a rare-earth magnet composed of an alloy containing one or more rare-earth elements. As one example, the magnetic material can be a neodymium magnet, such as $Nd_2Fe_{14}B$ ("NIB") or other alloys containing neodymium.

The bio-compatible shell 38 can be composed of gold; however, it will be appreciated that the bio-compatible shell 38 can also be composed of other bio-compatible metallic and non-metallic materials, including bio-compatible polymers. In some embodiments, the bio-compatible shell 38 includes more than one layer. As one example, the bio-compatible shell 38 can include an inner layer composed of nickel, a second layer composed of copper, a third layer composed of nickel, and a fourth, outer layer composed of diX® parylene-C (Kisco Ltd.; Japan).

In some examples, the magnetic seeds 12 can be sintered from rare-earth metals. The sintering method of manufacturing for the magnetic seeds 12 allows for a stronger magnetic flux distribution than alternative techniques; however, due to the small geometry of the magnetic seeds 12 and variance in materials, it is possible that the flux densities of the magnetic seeds 12 to fluctuate (e.g., by 4-6 percent). This inter-seed variability can be accounted for within the anisotropy and distance algorithms; however, this minimal variance is also generally acceptable for the purposes of the MOLLI guidance system of the present disclosure. It is also contemplated that constructing the magnetic seeds 12 to have radial symmetry will mitigate errors attributable to intra-seed variance.

The magnetic seeds 12 used in the present disclosure are generally constrained in geometry by the introducer needles that are used to implant the magnetic seeds 12 into the region-of-interest 14. As one example, for the magnetic seeds 12 to be inserted using standard sized needles commonly employed in radiology departments, the magnetic seeds 12 can be designed to have a diameter of 1.6 mm and a length of 3.2 mm along the longitudinal axis of the magnetic seed 12 (e.g., the cylindrical axis of the magnetic seed 12 illustrated in FIG. 2). This geometry enables the field strength of the magnetic seeds 12 to be maximized while still remaining practical to implant.

Figure 5:
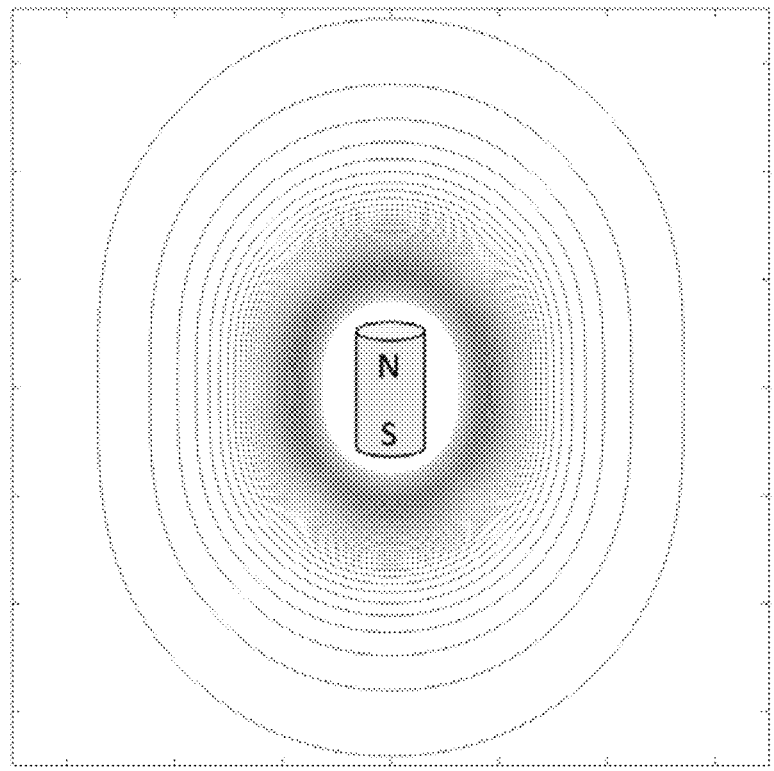
FIG. 5 is an example magnetic flux density diagram for a magnetic seed that generates an anisotropic magnetic field with an anisotropic magnetic flux density distribution.

The magnetic field generated by an anisotropic magnetic seed 12 is roughly similar in geometry to a conventional bar magnet. An example vector magnetic field distribution for a magnetic seed 12 is represented in FIG. 4, which demonstrates the perturbations and anisotropic response of the magnetic seed 12 construction. Notably, the vectors follow a toroidal pattern around the magnetic seed 12, which represents anisotropy in the magnetic field. This anisotropic effect is characterized and accounted for during detection of the magnetic seeds 12 such that the detector probe 18 can accurately discretize the distance to the magnetic seeds 12. FIG. 5 illustrates an example representation of the magnetic flux density of a magnetic seed 12 demonstrating a nonlinear and anisotropic distribution of the magnetic field. Each annular ring in FIG. 5 represents an increase in the strength of the flux density.

As shown in FIG. 5, the magnetic flux of the magnetic seeds 12 is not equivalent at the same distance axially versus radially. Because the system 10 calculates the distance of the magnetic seeds 12 from the detector probe 18 from the magnetic flux measured at the tip of the detector probe 18, the orientation of the magnetic seed 12 will influence the measurement of the distance between the magnetic seed 12 and the detector probe 18.

Thus, the anisotropic construction of the magnetic seeds 12 results in similar anisotropy in both their vector fields and flux density. This anisotropic effect can be quantified and this quantified information can be used in compensation algorithms to estimate the true distance between the tip of the detector probe 18 and a given magnetic seed 12. The uncertainty in those measurements can also be estimated and reported.

For example, the MOLLI system described here can evaluate the uncertainty in the calculation of the distance between the detector probe 18 and a given magnetic seed 12, and this information can then be displayed alongside a digital readout. It is contemplated that, for the example magnetic seed and detector probe designs described here, the magnitude of this error can vary between around 8 mm at the limit of magnetic seed detection (e.g., 7 cm from a magnetic seed) to less than 1 mm nearest a magnetic seed (e.g., 1 cm from a magnetic seed).

The estimation of the error in the seed-to-detector distance is dependent on the model used to account for the anisotropic construction of the magnetic seed 12. Simple look up tables are unable to accurately estimate the error in the seed-to-detector distances because they do not account for the physical construction of the magnetic seed 12. In these lookup-table approaches, the marker is assumed to be a single point in space with a homogenous magnetic field surrounding it, and thus no information about the structure of the marker is provided. Using lookup-tables with anisotropic magnetic seeds therefore does not allow for reliable estimation of the error in the distance of such magnetic seeds from a detector probe. As such, surgeons will not have confidence in the number that is presented.

The systems and methods of the present disclosure, however, incorporate a physical model of the magnetic seeds 12 into the detection of the magnetic seeds 12, and thus an uncertainty in those measurements can be accurately estimated and reported. Reporting a distance with an error estimate will provide confidence to the surgeon and will allow them to use this information in important clinical decision making.

As described above, the implanted magnetic seeds 12 are detected using a detector probe 18 that generally includes a first and second magnetic sensor 22, 24. As an example, the magnetic sensors 22, 24 can be magnetometers. In one example, the detector probe 18 is constructed such that the first magnetic sensor 22 is arranged at the proximal end of the detector probe 18 and such that the second magnetic sensor 24 is arranged at the distal end of the detector probe 18.

The detector probe 18 is designed to be insensitive to the Earth's magnetic field by using an in-built subtraction system that accounts for changes in the orientation of the detector probe 18 relative to the Earth's magnetic field. Although the magnetic sensors 22, 24 can be aligned along the central axis of the detector probe, in a preferred embodiment, one of the magnetic sensors can be offset from the central axis of the detector probe 18.

Figure 6:
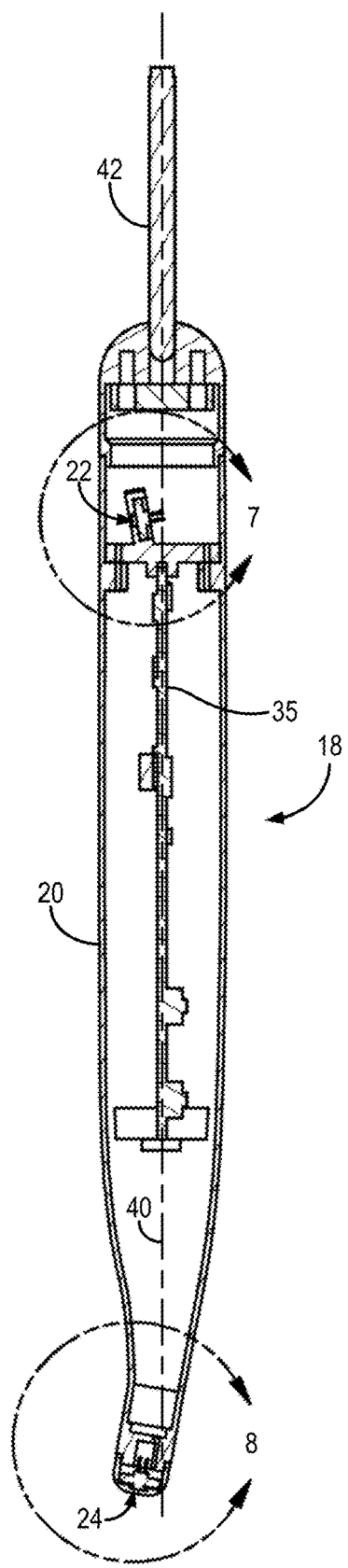
FIG. 6 is an example cross sectional view of a detector probe for detecting magnetic seeds implanted in a subject.
Figure 7:
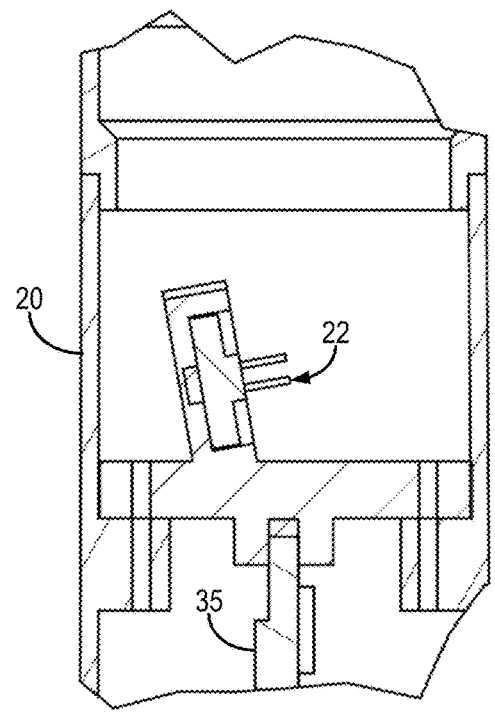
FIG. 7 is an example cutaway view of the distal end of the detector probe of FIG. 6.
Figure 8:
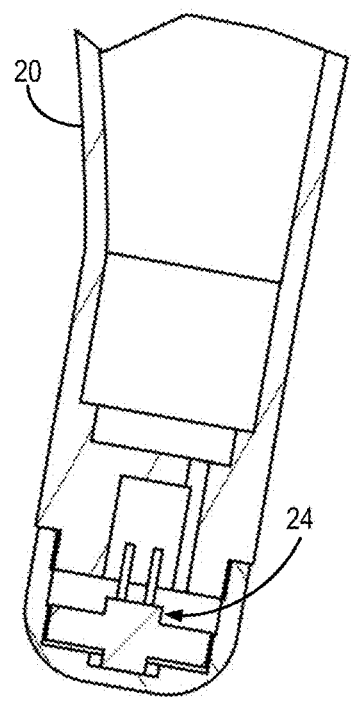
FIG. 8 is an example cutaway view of the proximal end of the detector probe of FIG. 6.

As one example, the second magnetic sensor 24 can be offset to provide a more ergonomic design of the detector probe 18. Such an arrangement is illustrated in FIGS. 6-8, which show a detector probe 18 in which the first magnetic sensor 22 and the second magnetic sensor 24 are not coaxial with the central axis 40 of the detector probe 18. Because of the built-in ability to compensate for the Earth's magnetic field, unlike previous magnetic detector systems, the detector probe 18 does not have strict requirements or constraints on the alignment of the magnetic sensors 22, 24 with respect to each other and other arrangements and alignments of the magnetic sensors 22, 24 can be readily adapted.

The detector probe 18 is in electrical communication with the computer system 26, as described above, via a cable 42 located at the distal end of the detector probe 18. The cable 42 can include one or more electrical wires, and can also include one or more optical fibers. In general, the cable 42 provides electrical power to the detector probe 18 and also provides for communication of signal data measured by the magnetic sensors 22, 24 to the computer system 26. In some other embodiments, the detector probe 18 can be in wireless communication with the computer system 26, in which the cable 42 can be removed. Power can be provided to the detector probe 18 via an internal battery in these configurations. In other embodiments, the computer system 26 can be housed within the housing 20 of the detector probe 18. For instance, as shown in FIG. 6, the computer system 26 can include a printed circuit board one which a hardware processor and a memory are arranged. In such configurations, the computer system 26 can be powered via cable 42, or via an internal battery.

During operation, or before operation, of the detector probe 18, the computer system 26 can perform a calibration procedure, in which each magnetic sensor 22, 24 is independently calibrated. The measurements provided by the magnetic sensors 22, 24 can then be fused to compensate for any misalignment. Through this calibration procedure, the magnetic sensors 22, 24 are placed in a common coordinate system, such that the location of the magnetic sensors 22, 24 is known relative to a common spatial reference point. These calibration values can be stored as calibration data in the computer system 26 for subsequent use by the computer system 26 and detector probe 18. The detector probe 18 can be independently serially numbered and calibrated and the corresponding calibration data for the magnetic sensors 22, 24 can be stored in a memory (e.g., a non-volatile memory) contained within the detector probe 18. In some instances, the computer system 26 can be contained within the detector probe 18 and the memory can form a part of the computer system 26.

Figure 9:
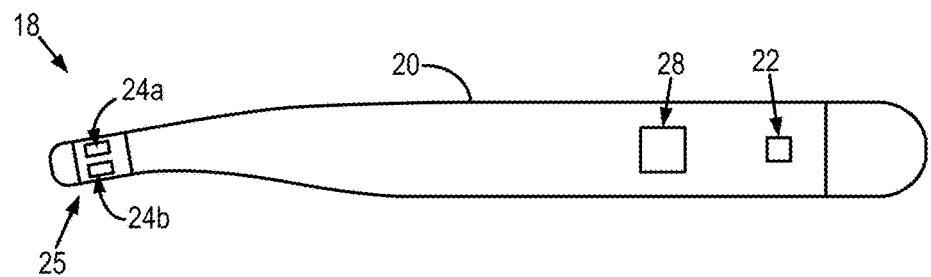
FIG. 9 is an example of a detector probe having an array set of magnetic sensors at its distal end and a single magnetic sensor at its proximal end.

Although FIGS. 6-8 depict a detector probe 18 with only two magnetic sensors 22, 24, the detector probe 18 can be constructed to have more than two magnetic sensors. In some examples, more than two magnetic sensors can be arranged within the housing 20 of the detector probe 18, while in other examples, one or more additional magnetic sensors can be affixed or otherwise arranged on the outer surface of the housing 20. As one non-limiting example, the detector probe 18 can include one or more arrays of magnetic sensors. For instance, the detector probe 18 could include an array set of two distal magnetic sensors 24a, 24b, and one proximal magnetic sensor 22, as illustrated in FIG. 9. Other sensors can also be arranged within the housing 20 of the detector probe 18 or on the outer surface of the housing 20. Examples of such other sensors include accelerometers, gyroscopes, and so on. One or more of the magnetic sensors 22, 24 can also be replaced with an array of such sensors.

By utilizing one or more arrays of magnetic sensors, or other sensors (e.g., accelerometers, gyroscopes) the direction from a magnetic seed 12 and the detector probe 18 can be determined and visualized. With the capability of measuring the directionality of the magnetic seeds 12 relative to the detector probe 18, a digital collimation effect can be provided and switched on or off as desired by the clinician. When activated, the collimation will only provide an auditory or visual cue to the clinician when a magnetic seed 12 is within a viewing window of the tip of the detector probe 18. Outside of this viewing window, the detector probe 18 will not trigger an auditory or visual cue, even if a magnetic seed 12 is detected as outside of that viewing window. This functionality allows the MOLLI system 10 to closely replicate the use and function of RSL probes.

The detector probe 18 is capable of resolving depth and can achieve a spatial resolution that is sufficient to detect and resolve magnetic seeds 12 that are close to each other. This capability allows for bracketing the region-of-interest 14 with magnetic seeds 12, which is not possible with radio-active seeds.

As mentioned above, the MOLLI system 10 can operate with feedback from only two magnetic sensors 22, 24. It is contemplated that with only two magnetic sensors 22, 24, and no other sensors, the MOLLI system 10 can achieve a sensitivity and specificity of 95 percent at a depth of detection of 70 mm.

The MOLLI system 10 is designed to help expeditiously guide a surgeon to a magnetic seed 12 with relative ease. To help achieve this goal, the localization attainable by the MOLLI system 10 is accurate and precise, with a spatial resolution that is comparable or better than that of gamma probes used in radio-seed localization.

The introducer device 34 can be used to provide the magnetic seeds 12 to a location in the subject 16. Preferably, the introducer 34 is composed of a non-magnetic material, such that the magnetic seeds 12 can be accurately positioned without interacting with the introducer device 34.

Figure 10:
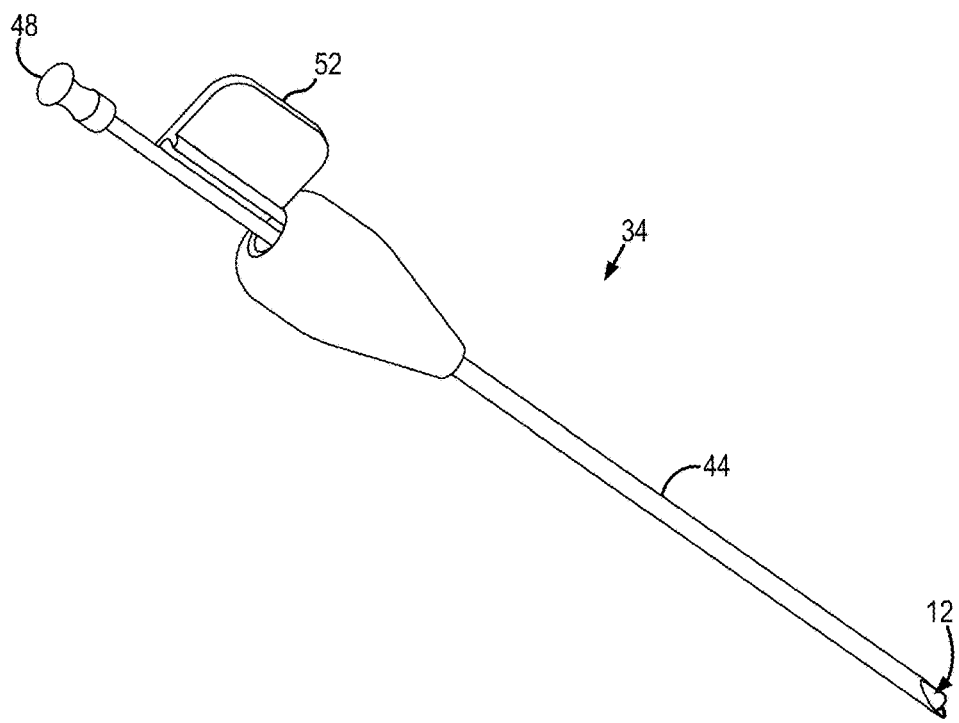
FIG. 10 is an example of an introducer device for implanting a magnetic seed in a subject.
Figure 11:
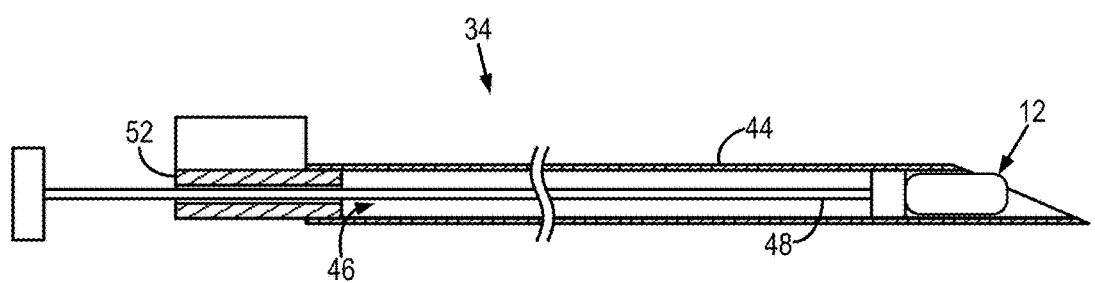
FIG. 11 is a cross sectional view of the introducer device of FIG. 9.

As shown in FIGS. 10 and 11, the introducer device 34 generally includes a needle 44 having a lumen 46 that is sized to receive a magnetic seed 12. In some embodiments, the lumen 46 is sized to be sufficiently larger than the magnetic seed 12 such that an air tight seal is not achieved when the magnetic seed 12 is positioned in the lumen 46 of the needle 44.

The needle 44 is preferably composed of a non-magnetic material, as mentioned above. As one example, the needle 44 can be composed of titanium or a suitable titanium alloy. As another example, the needle 44 can be composed of stainless steel or a suitable stainless steel alloy. The needle 44 can also be composed of other magnetically inert metals, plastics, or so on.

A plunger 48 is located at the distal end of the needle 44 and is sized to be received by the lumen 46 of the needle 44. The plunger 48 is in fluid communication with the magnetic seeds 12, such that operation of the plunger 48 provides a force the pushes the magnetic seed 12 out of the lumen 46 at the open tip of the needle 44. The plunger 48 is also sized such that when it is retracted in the lumen 46 after deploying a magnetic seed 12, air is allowed to pass freely in the lumen 46, thereby eliminating a vacuum effect that could otherwise interfere with the accurate placement of the magnetic seed 12. In some other embodiments, the plunger 48 is sized to have an air tight fit with the inner surface of the lumen 46, but a hole is formed in the plunger 48 such that air can flow past the plunger 48 to avoid creating a vacuum effect that could interfere with accurate placement of the magnetic seeds 12.

In some embodiments, the plunger 48 and needle 44 are constructed such that in use the plunger 48 is held in place while the needle 44 is retracted to place a magnetic seed 12. In these embodiments, the plunger 48 is preferably designed to hold the magnetic seed 12 in place while the needle 44 is retracted. In some other embodiments, a lock 52 or other suitable retaining device is used to constrain the plunger 48 within the lumen 46 of the needle 44. The lock 52 can be composed of silicone or other malleable rubber, plastic, or synthetic material.

In some configurations, the tip of the needle 44 can be sealed using bone wax or another suitable bio-compatible and bio-degradable material, so as to provide a temporary closure at the tip of the needle 44 that disallows the magnetic seeds 12 to exit the lumen 46 without operation of the plunger 48.

The MOLLI system 10 generally operates by interrogating the volume around the tip of the detector probe 18 for a magnetic seed 12. The magnetic flux of magnetic seed 12 is then measured and an algorithm used to determine the distance of the magnetic seed 12 from the tip of the detector probe 18. This algorithm corrects and accounts for the anisotropy of the magnetic seeds 12, as mentioned above, by incorporating a physical model of the magnetic seeds 12 into the calibration and detection algorithms. The distance calculation is the primary method of feedback for the surgeon as it is correlated to both the visual display, auditory feedback, and actual units displayed. As described above, directionality can also be measured and displayed to the surgeon.

In addition to providing the distance from the tip of the detector probe 18 to an implanted magnetic seed 12, the MOLLI system 10 of the present disclosure is able to determine the distance and quantify the error in the distance measurement, which is described above. This capability of the MOLLI system 10 allows for the completeness of a surgery to be evaluated by ensuring that the cut edge of an excised specimen is at a specified distance from the magnetic seeds 12, which enables the surgeon to plan the margin and grossly evaluate whether this margin was achieved intraoperatively. This intraoperative margin evaluation can reduce the incidence of re-excision in breast conserving surgeries. The margin evaluation method can also alert the surgeon to an area on their excised volume where the distance to the magnetic seed is less than the average, thereby allowing the surgeon to re-excise that portion of the surgical cavity to better ensure that a clear surgical margin can be achieved.

Conventional wire-guided localization used in breast conserving surgeries is often used to mark diffuse disease. In these circumstances, two wires may be located to mark the extent of disease and signify to the surgeon that the region between the two wires is the target area. Additionally, the indexes on the wire are also used to indicate that the region between a specific marker and the end of the wire should be removed.

The popularization of RSL has led to the use of iodione-125 marker seeds to localize a lesion for removal in a similar fashion to the original intent of wire-guided localizations. In recent years "bracketing" has become an additional use of RSL seeds to identify the broad regions that a radiologist has identified as suspicious and necessary for removal.

Conventionally, bracketing is utilized when the extent of disease will not be readily apparent to the surgical team. As an example, a clinically representative distance for bracketing is on the order of 50-70 mm. It is contemplated that the spatial resolution attainable with the MOLLI system 10 of the present disclosure will allow localization of magnetic seeds 12 as close as 10 mm. As such, there is little interaction between magnetic seeds 12 separated by clinically representative distances of greater than 40 mm, thereby allowing for bracketing to be implemented with the MOLLI system 10.

The ability to identify the extent of disease with multiple magnetic seeds 12 prior to surgery is desirable. This ability will allow the surgeon to plan the procedure in order to completely excise the tumor with minimal excision of normal tissue. The MOLLI system 10 is capable of differentiating magnetic seeds spaced apart by 10 mm or more at 2 cm depth; as such, the MOLLI system 10 enables bracketing of lesions. Lesions that are smaller than 1 cm do not typically require bracketing given their limited volume.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for localizing a magnetic seed that generates a magnetic field, comprising:
   moving a detector probe towards the magnetic seed until a first magnetic sensor and a second magnetic sensor each detect a magnetic field generated by the magnetic seed and in response thereto generate signal data representative of the magnetic field, wherein the detector probe comprises a housing with a proximal portion and a distal tip portion, the distal tip portion is angled with respect to the proximal portion, the first magnetic sensor is located in the proximal portion, the second magnetic sensor is located in the distal tip portion, an operative sensor axis of the first magnetic sensor is not parallel with an operative sensor axis of the second magnetic sensor, the operative sensor axis of the second magnetic sensor is not parallel with a central axis of the proximal portion, and at least one of the first magnetic sensor and the second magnetic sensor is arranged in the housing to be offset from the central axis of the proximal portion;
   receiving, at a processor, the signal data of the first magnetic sensor and the second magnetic sensor;
   processing the signal data to compute a location of the magnetic seed, wherein processing the signal data includes accounting for an anisotropic geometry of the magnetic field generated by the magnetic seed; and
   providing an output signal based on the computed location of the magnetic seed.

2. The method of claim 1, further comprising calibrating the first magnetic sensor and the second magnetic sensor independent from each other based on a known spatial relationship between the first magnetic sensor, the second magnetic sensor, and the Earth's magnetic field.

3. The method of claim 2, wherein calibrating the first magnetic sensor and the second magnetic sensor subtracts effects of the Earth's magnetic field in the signal data received by the processor from the first magnetic sensor and the second magnetic sensor.

4. The method of claim 2, wherein calibrating the first magnetic sensor and the second magnetic sensor generates calibration data that are stored in a memory.

5. The method of claim 1, wherein the processor accounts for the anisotropic geometry of the magnetic field generated by the magnetic seed by using a physical model of the magnetic seed when estimating a distance of the magnetic seed from the detector probe.

6. The method of claim 1, wherein at least one of the first magnetic sensor and the second magnetic sensor is a magnetometer.

7. The method of claim 1, wherein at least one of the first magnetic sensor and the second magnetic sensor comprise an array of magnetometers.

8. The method of claim 7, wherein the array of magnetometers define a viewing window and the processor computes the location of the magnetic seed only when the magnetic seed is located within a volume define by the viewing window.

9. The method of claim 1, wherein each of the first magnetic sensor and the second magnetic sensor excludes an accelerometer component.

10. The method of claim 1, wherein the detector probe comprises the first magnetic sensor and the second magnetic sensor and no other sensors.

* * * * *